US008592439B2

(12) United States Patent
Cavazza et al.

(10) Patent No.: US 8,592,439 B2
(45) Date of Patent: Nov. 26, 2013

(54) LONG-TERM TREATMENT OF SYMPTOMATIC HEART FAILURE

(75) Inventors: Claudio Cavazza, Rome (IT); Maria Giovanna Caccia, Rovellasca (IT)

(73) Assignees: SpA Societa Prodotti Antibiotici S.p.A., Milan (IT); Sigma-Tau Industrie Farmaceutiche Riunite S.p.A., Rome (IT)

( * ) Notice: Subject to any disclaimer, the term of this patent is extended or adjusted under 35 U.S.C. 154(b) by 189 days.

(21) Appl. No.: 13/057,492

(22) PCT Filed: Jul. 23, 2009

(86) PCT No.: PCT/EP2009/005347
§ 371 (c)(1),
(2), (4) Date: Apr. 5, 2011

(87) PCT Pub. No.: WO2010/015335
PCT Pub. Date: Feb. 11, 2010

(65) Prior Publication Data
US 2011/0178111 A1    Jul. 21, 2011

(30) Foreign Application Priority Data

Aug. 7, 2008 (EP) ..................... 08161994

(51) Int. Cl.
*A61K 31/505* (2006.01)
(52) U.S. Cl.
USPC ............ 514/275; 514/560; 514/460; 514/419
(58) Field of Classification Search
USPC .................................. 514/275, 560, 460, 419
See application file for complete search history.

(56) References Cited

U.S. PATENT DOCUMENTS

| 5,541,225 A * | 7/1996 | Leaf et al. ..................... 514/560 |
| 7,462,643 B1 * | 12/2008 | Pamparana .................... 514/549 |
| 2006/0135610 A1 * | 6/2006 | Bortz et al. ................... 514/548 |

FOREIGN PATENT DOCUMENTS

WO    WO2008/063323    *  5/2008

OTHER PUBLICATIONS

Hoskins et al., Future Lipidology, 2006, 1(5): 579-591.*
Marchioli et al., "Dietary supplementation with n-3 polyunsaturated fatty acids and vitamin E after myocardial infarction: results of the GISSI-Prevenzione trial" The Lancet, vol. 354, 1999, pp. 447-455.
Marchioli et al., "Assessment of absolute risk of death after myocardial infarction by use of multiple-risk-factor assessment equations" European Heart Journal, vol. 22, 2001, pp. 2085-2103.
Tavazzi et al., "Rationale and design of the Gissi heart failure trial: a large trial to assess the effects of n-3 polyunsaturated fatty acids and rosuvastatin in symptomatic congestive heart failure" The European Journal of Heart Failure, vol. 6, 2004, pp. 635-641.
Kowalski et al., "Do N-3 Polysunsaturated Fatty Acids Reduce Risk of Sudden Cardiac Death and Ventricular Arrhythmias? A Meta-analysis of Randomized Trials" Circulation, vol. 114, No. 18, Oct. 2006, p. 892 (Abstract).
Brouwer et al., "SOFA: Study of omega-3 fatty acids and ventricular arrhythmia. A multicenter, randomized clinical trial" Circulation, vol. 113, No. 8, Feb. 2006, p. E371 (Abstract).
Fauchier et al., "N-3 polyunsaturated fatty acids and major arrhytmic events: a meta-analysis of randomized controlled trials" Journal of the American College of Cardiology, vol. 49, No. 9, Mar. 2007, p. 38A (Abstact).
Lombardi et. al., "Anti-arrhythmic properties of n-3 polyunsaturated fatty acids (n-3 PUFA)" Current Medicinal Chemistry, vol. 14, 2007, pp. 2070-2080.
Jenkins et al., "Heterogeneity in Randomized Controlled Trials of Long Chain (Fish) Omega-3 Fatty Acids in Restenosis, Secondary Prevention and Ventricular Arrhythmias" Journal of the American College of Nutirion, vol. 27, No. 3, Jun. 2008, p. 367-378.

* cited by examiner

*Primary Examiner* — Rei-tsang Shiao
(74) *Attorney, Agent, or Firm* — Lucas & Mercanti, LLP

(57) ABSTRACT

The main object here is the use of omega-3 polyunsaturated fatty acids (as ethyl esters, hereinafter called "n-3 PUFA") as a medicament, either alone or in combination with other therapeutic agents, for reducing mortality for a cardiovascular cause, in particular arrhythmia or for reducing hospitalization for any cause, in particular a cardiovascular cause and for the daily administration to patients with symptomatic heart failure (HF) for more than 3.5 years.

9 Claims, 3 Drawing Sheets

LONG-TERM TREATMENT OF SYMPTOMATIC HEART FAILURE

This application is a U.S. national stage of PCT/EP2009/005347 filed on Jul. 23, 2009 which claims priority to and the benefit of European Application No. 08161994.2 filed on Aug. 7, 2008, the contents of which are incorporated herein by reference.

FIELD OF THE INVENTION

The present invention relates to the use of omega-3 polyunsaturated fatty acids (as ethyl esters, hereinafter called "n-3 PUFA") as a medicament, either alone or in combination with other therapeutic agents, for reducing mortality for a cardiovascular cause, in particular arrhythmia or for reducing hospitalization for any cause, in particular a cardiovascular cause and for the daily administration to patients with symptomatic heart failure (HF) for more than 3.5 years.

BACKGROUND OF THE INVENTION

Heart failure is a condition that can result from any structural or functional cardiac disorder that impairs the ability of the heart to fill with blood or pump a sufficient amount of blood through the body. It is not to be confused with "cessation of heartbeat", which is known as asystole, or with cardiac arrest, which is the cessation of normal cardiac function with subsequent hemodynamic collapse leading to death.

Congestive heart failure is often undiagnosed due to a lack of a universally agreed definition and difficulties in diagnosis, particularly when the condition is considered "mild". Even with the best therapy, heart failure is associated with an annual mortality of 10%. It is the leading cause of hospitalization in people older than 65.

Heart failure is characterized by clinical signs and symptoms secondary to the inadequate response to the body metabolic requirements. This condition could occur acutely or have a chronic course.

The pathophysiological interpretations of heart failure have had a remarkable evolution in time. This syndrome was considered as a pump deficiency associated with a renal dysfunction in years '50-'60, a pump dysfunction associated with an increase in peripheral resistance in years '70-'80 and is considered at present as a failure of the pump function associated with the neuro-hormonal activation with resulting hemodynamic impairments which take to a dysfunction of many organs and apparatuses.

The present drug therapy of cardiac "pump function" includes the use of drugs acting by various modes of action on different points of the etiopathogenesis of the diseases.

Non-limiting examples of such drugs are: ACE-inhibitors (Angiotensin Converting Enzymes inhibitors), diuretics, non-digitalis positive inotropic drugs such as adrenergics and inhibitors of phosphodiesterase, arteriolar and venular vasodilators, e.g. hydralazine and isosorbide dinitrate, beta-blockers e.g. metoprolol and bisoprolol and digitalis derivatives, e.g. digitoxin.

The ageing of the population seems to be a contributing factor to amplify the relevance of the phenomenon.

WO 02/058793 relates to the use of polyunsaturated fatty acid for the prevention or treatment of heart failure. No experimental data are provided in this application.

Lancet 1999 (354: 447-55) (GISSI-Prevenzione clinical trial) relates to the reduction of total mortality in post-myocardial infarction patients treated with n-3 PUFA for 3.5 years.

EP1310249 relates to the use of polyunsaturated fatty acid for the primary prevention of major cardiovascular events in patients, who have not undergone previous infarct episodes. However only some animal data are reported in the patent application and these are not necessarily predictive of the drug efficacy in the treatment of HF in humans.

WO 89/11521 describes an industrial process for the extraction of mixtures having a high content in poly-unsaturated acids useful in the treatment of cardiovascular pathologies.

U.S. Pat. No. 5,502,077, U.S. Pat. No. 5,656,667, U.S. Pat. No. 5,698,594 and IT 1235879, refer respectively to hyper-triglyceridemia, defects of the cholesterol level and hypertension. However, each of the cited documents deal with the treatment of risk factors, not with real and proclaimed illnesses.

U.S. Pat. No. 5,753,703 describes the use of L-carnitine or its derivatives in association with polyunsaturated fatty acids of the omega-3 series or their esters, in particular EPA and DHA, for the prevention and treatment of cardiovascular disorders, vascular pathologies, diabetic peripheral neuropathies, and atherosclerotic, thromboembolytic and tissue disorders.

EP0409903 describes a process for preparing high concentration mixtures of EPA and DHA and/or their esters useful for treating hyperlipemia and related pathologies, thrombosis, cardiac infarct, platelet aggregation, as anticoagulants in the prevention of atherosclerosis, for the treatment of cerebral infarct, of lesions and occlusions caused by vasomotor spasms, of diabetes and its complications, of chronic and acute inflammations, of autoimmune symptoms, in the prevention of side effects caused by non-steroid anti-inflammatories at the gastrointestinal level and in tumour prevention.

CN 1082909 describes compositions based on ethyl esters of EPA and DHA and other polyunsaturated fatty acids of the omega-3 series in association with soya phospholipids, oenothera odorata and ginkgetin, as antithrombotic and anti-dementia agents for treating for example dementia and infarct of the myocardium.

U.S. Pat. No. 5,760,081 describes a method for preventing imminent fibrillation of the myocardial ventricle by intravenous infusion of a composition containing EPA, where the subject at risk of imminent fibrillation has already often been the protagonist of an episode of infarct of the myocardium and where the infusion is effected within 3 hours of the infarct episode, possibly using intracardiac injection. These are always situations of extreme emergency and of parenteral intervention, for the specific treatment of ventricular fibrillation.

Clinical Drug Investigation 15 (6), 473 relates to the administration of EPA and DHA ethyl esters, at a dose of 4 g per day for decreasing triglycerides and total apolipoprotein C III and increasing antithrombin III, in subjects with abnormal plasmatic lipoprotein symptoms and have undergone an infarct of the myocardium, they having consequently suggested that an administration of these compositions can result in an improvement in the lipoprotein level and hence a decrease in the relative risk factors.

WO 00/48592 describes the use of a mixture of EPA and DHA ethyl esters in quantities greater than 25% b.w., for preventing death, in particular "sudden death" in patients who have already suffered an infarct of the myocardium.

In the medical field there is still the need of a safe and convenient method for the prevention of deaths, the reduction of the total hospitalisations or the hospitalisations for a cardiovascular reason in patients with heart failure.

DESCRIPTION OF THE INVENTION

In a large-scale clinical trial it has now been found that patients with symptomatic heart failure (HF) treated for more than 3.5 years with n-3 PUFA showed a statistically significant reduction of:
- the number of deaths for a cardiovascular cause, in particular arrhythmia;
- the number of hospitalisations for any cause; and
- the number of hospitalisations for a cardiovascular cause, in particular the number of first hospitalisations for ventricular arrhythmias.

Moreover a predefined subgroup analysis has also showed that patients having left ventricular ejection fraction <40% (LVEF <40%), diabetes and/or total cholesterol <200 mg/dl, preferably ≤188 mg/dl, showed a statistically significant reduction of a combination of deaths for any cause and hospitalisations for a cardiovascular cause.

These results are surprising and unexpected, because the prior art never mentioned nor suggested said specific achievements. In fact, for example, in Lancet 1999 (354: 447-55) or in European Heart Journal 2000 (21; 949-952) the rate of non-fatal cardiovascular events (non-fatal myocardial infarction and non fatal stroke) was reported as being unchanged by n-3 PUFA treatment.

It is therefore the main object of the present invention the use of n-3 PUFA as a medicament, either alone or together with other therapeutic agents, for:
- preventing mortality for a cardiovascular cause, in particular arrhythmia;
- reducing hospitalisation for any cause; or
- reducing hospitalisation for a cardiovascular cause, in particular reducing the risk of first hospitalisation for ventricular arrhythmias;

and for the administration for more than 3.5 years to patients with symptomatic HF.

One preferred embodiment of the present invention is the use of n-3 PUFA as a medicament, either alone or together with other therapeutic agents, for reducing mortality or hospitalisation for a cardiovascular cause and for the administration for more than 3.5 years to patients with symptomatic HF having left ventricular ejection fraction <40% (LVEF <40%), diabetes and/or total cholesterol <200 mg/dl, preferably ≤188 mg/dl.

It is therefore a further object of the present invention the use of n-3 PUFA for the preparation of a medicament, either alone or together with other therapeutic agents, useful for:
- preventing mortality for a cardiovascular cause, in particular arrhythmia;
- reducing hospitalisation for any cause; or
- reducing hospitalisation for a cardiovascular cause, in particular reducing the risk of first hospitalisation for ventricular arrhythmias;

and for the administration for more than 3.5 years to patients with symptomatic HF.

A further preferred embodiment of the present invention is the use of n-3 PUFA for the preparation of a medicament, either alone or together with other therapeutic agents, useful for reducing mortality or hospitalisation for a cardiovascular cause and for the administration for more than 3.5 years to patients with symptomatic HF having left ventricular ejection fraction <40% (LVEF <40%), diabetes and/or total cholesterol <200 mg/dl, preferably ≤188 mg/dl.

The term "n-3 PUFA" (also referred to as ω-3 fatty acids or omega-3 fatty acids) relate to a family of long-chain polyunsaturated fatty acids, generally $C_{16}$-$C_{24}$, in particular those having a $C_{20}$-$C_{22}$ chain, that have in common a carbon-carbon double bond in the n-3 position, i.e. the third bond from the methyl end of the fatty acid. Examples of the most common n-3 fatty acids found in nature are reported in the Table below together with the assigned names.

| Common name | Lipid name | Chemical name |
| --- | --- | --- |
| — | 16:3 (n-3) | all-cis-7,10,13-hexadecatrienoic acid |
| α-Linolenic acid (ALA) | 18:3 (n-3) | all-cis-9,12,15-octadecatrienoic acid |
| Stearidonic acid (STD) | 18:4 (n-3) | all-cis-6,9,12,15-octadecatetraenoic acid |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic acid (EPA) | 20:5 (n-3) | all-cis-5,8,11,14,17-eicosapentaenoic acid |
| Docosapentaenoic acid (DPA), Clupanodonic acid | 22:5 (n-3) | all-cis-7,10,13,16,19-docosapentaenoic acid |
| Docosahexaenoic acid (DHA) | 22:6 (n-3) | all-cis-4,7,10,13,16,19-docosahexaenoic acid |
| Tetracosapentaenoic acid | 24:5 (n-3) | all-cis-9,12,15,18,21-docosahexaenoic acid |
| Tetracosahexaenoic acid (Nisinic acid) | 24:6 (n-3) | all-cis-6,9,12,15,18,21-tetracosenoic acid |

Preferably the n-3 PUFA according to the invention is a mixture of fatty acids having a high content in EPA and DHA, for example with a content in EPA and DHA higher than 25% by weight, preferably from about 30% to about 100% by weight, in particular about between 75% and 95%, and more preferably at least 85% by weight on the total fatty acid weight. Preferably the total content of n-3 PUFA according to the invention is a mixture of fatty acids having at least 90% of n-3 PUFA by weight on the total fatty acid weight.

The term "n-3 PUFA" as used here is intended to encompass their corresponding $C_1$-$C_3$ alkyl esters and/or from their salts with pharmaceutically acceptable bases such as sodium hydroxide, lysine, arginine or aminoalcohols such as choline. The ethyl esters are the most widely used and preferred according to the invention.

The composition of the invention is administered preferably orally, in particular in the form of soft gelatin capsules. For oral use, the unit dose generally comprises 100-1000 mg of polyunsaturated fatty acids of the omega-3 series, preferably 500-1000 mg or 300-500 mg, the total dose being usually around 0.1-3.0 g per day or per alternate day, according to the case concerned, and preferably 0.3-2.0 g per day and in particular 1.0 g per day.

This amount of product may be administered in the form of several daily divided doses or preferably as a single dose, in order to reach the desired blood level. Of course, the clinician may vary the amount of product (or mixture with another therapeutic agent) to be administered, basing on the patient's conditions, age and weight.

Other types of formulation for oral administration are also suitable for the purposes of the invention; for example hard capsules or tablets, in which the polyunsaturated fatty acids are adsorbed on solid supports. It is also possible to use emulsions, granulates in dispersing excipients, syrups, droplets, etc., and other forms of administration able to ensure systemic absorption of the drug, such as sterile solutions or emulsions and the like, suitable for parenteral use and the like, as evaluated by the expert of the art, on the basis of the severity of the pathology.

Those compositions illustrated in the European Pharmacopea 2000 (EuPh. 2000), containing quantities greater than or equal to 80 wt % of mixtures of EPA and DHA ethylesters and a total of omega-3 polyunsaturated fatty acid ethyl esters greater than or equal to 90 wt % are also suitable for the purposes of the present invention.

The drug suitable for use according to the present invention generally comprise at least one pharmaceutically acceptable vehicle and/or one diluent and/or one surfactant and/or one thickener and/or one binder and/or one lubricant and/or one aromatizer and/or one colorant and/or one stabilizer and the like, which can easily be selected by the expert of the art.

The following Table reports non limiting examples of n-3 PUFA compositions, that can be used according to the present invention.

| | N-3 PUFA COMPOSITIONS | | | |
|---|---|---|---|---|
| | 1 | 2 | 3 | 4 |
| Total ethyl esters of polyunsaturated fatty acids | | 1000 mg | | |
| EPA ethyl ester | 525 mg | 525 mg | | >400 mg |
| DHA ethyl ester | 315 mg | 315 mg | | >340 mg |
| EPA + DHA ethyl ester | | | 850 mg | >800 mg |
| Total mega-3 ethyl ester | | | | >900 mg |
| D-alpha-tocopherol | 4 I.U. | 4 I.U. | | 4 I.U. |
| D,L-alpha-tocopherol | | | 0.3 mg | |
| gelatin | 246 mg | 246 mg | | 246 mg |
| gelatin succinate | | | 233 mg | |
| glycerol | 118 mg | 118 mg | 67 mg | 118 mg |
| yellow iron oxide | 1.27 mg | 1.27 mg | | 1.27 mg |
| red iron oxide | 2.27 mg | 2.27 mg | | 2.27 mg |
| sodium p-hydroxy-benzoate | | | 1.09 mg | |
| sodium propyl p-hydroxy-benzoate | | | 0.54 mg | |

I.U. = International Unit.

The most preferred ratio between EPA and DHA is about 0.6-1.1/1.3-1.8; in particular is comprised between 0.9 and 1.5.

Preferably the content of EPA (as ethyl ester) is comprised between 40 and 51% by weight and the content of DHA (as ethyl ester) is comprises between 34 and 45% by weight on the total fatty acids weight.

Specific drugs containing n-3 PUFA that meet the above specifications, as active ingredient and that can be used according to the present invention, are already available on the market.

The term "another therapeutic agent" means an additional single agent or two or more additional agents, preferably from 2 to 10, in particular from 2 to 6 according to physician's instructions, which may be administered in combination, namely either along or separately (substantially simultaneously or sequentially) with the n-3 PUFA.

Examples of therapeutic agents for such a prophylaxis or combined therapy according to the invention are ACE-inhibitors, NEP-inhibitors, ACE/NEP-inhibitors, angiotensin I converting enzyme inhibitors, diuretics, positive inotropic drugs, phosphodiesterase inhibitors, arteriolar and venular vasodilators, beta-blockers and digitalis glycosides, or a mixture thereof.

NEP means degradation peptidase of atrial natriuretic peptide (ANP).

Examples of ACE-inhibitors are: captopril, enalapril, lisinopril, fosinopril, cilazapril, benazapril, perindopril, quinapril, ramipril, trandolapril and delapril, in particular cilazapril, captopril and enalapril.

Examples of ACE/NEP-inhibitors are: omapatrilat, sampatrilat and L-phenylalanine, [(2S)-2-(mercaptomethyl)-1-oxo-3-phenylpropyl]-4-(2-thiazolyl) (compound Z13752A, a product of Zambon Company).

Examples of angiotensin II receptors antagonists (angiotensin II converting inhibitors) are: candesartan, valsartan and losartan.

Examples of diuretics are: hydrochlorothiazide, trichlormethiazide, chlorothiazide, chlortalidone, triamterene, clofenamide, furosemide, torasemide, ethacrynic acid, etozoline, spironolactone and amiloride, if the case in association with potassium sparing drugs, which are well known in the art, in particular furosemide and hydrochlorothiazide.

Examples of dopaminergic agents are dopamine and ibopamine.

Examples of phosphodiesterase inhibitors are: aminone, milrinone, enoximone and bucladesine, in particular aminone and enoximone.

Examples of arteriolar and venular vasodilators are: hydralazine and isosorbide dinitrate.

Examples of beta-blockers are: visoprolol, practotol, metoprolol, bucindol, carvedilol, atenolol, bisoprolol, celiprolol and nevibolol, in particular visoprolol, carvedilol and metoprolol.

Examples of digitalis glycoside agents are: acetyl digitoxin, acetyldigoxin, digitoxin, digoxin, lanatoside C, deslanoside, methyldigoxin and gitoformat, in particular digitoxin, digoxin, acetyldigoxin and metidigoxin.

Examples of positive inotropic agents are: pimobendan and vesnarinone, in particular pimobendan.

Another therapeutic agent that may be used according to the invention is a statin. The statin that can be used according to the present invention is any statin known for human use. A non limiting example is a statin selected from the group consisting of simvastatin, lovastatin, fluvastatin, pravastatin, atorvastatin, cerivastatin, rovastatin and rosuvastatin, preferred are simvastatin and rosuvastatin.

The preferred dose of n-3 PUFA to be administered to a patient with HF according to the invention is a 1 g oral daily dose and the duration of the treatment is longer than 3.5 years, preferably at least 4 years.

The preferred dose of a statin to be administered to a patient with HF in combination with n-3 PUFA according to the invention is a 10 mg oral daily dose and the duration of the treatment is longer than 3.5 years, preferably at least 4 years.

The term "hospitalisation" as used here means number of admissions to hospital for each patient.

The wording "patient with symptomatic heart failure (HF)" as used here means a man or a woman with clinical evidence of HF (heart failure) of any etiology classified according to the European Society of Cardiology guidelines as NYHA class II-IV (New York Heart Association Classification).

In cardiovascular physiology, ejection fraction is the fraction of blood pumped out of a ventricle with each heart beat. The term ejection fraction applies to both the right and left ventricles. Without a qualifier, the term ejection fraction refers specifically to that of the left ventricle, therefore it is synonym of left ventricular ejection fraction (LVEF).

Healthy individuals typically have ejection fractions greater than 55%. Damage to the muscle of the heart, such as that experienced during myocardial infarction or in cardiomyopathy, impairs the heart's ability to eject blood and therefore reduces ejection fraction.

Figure 1:
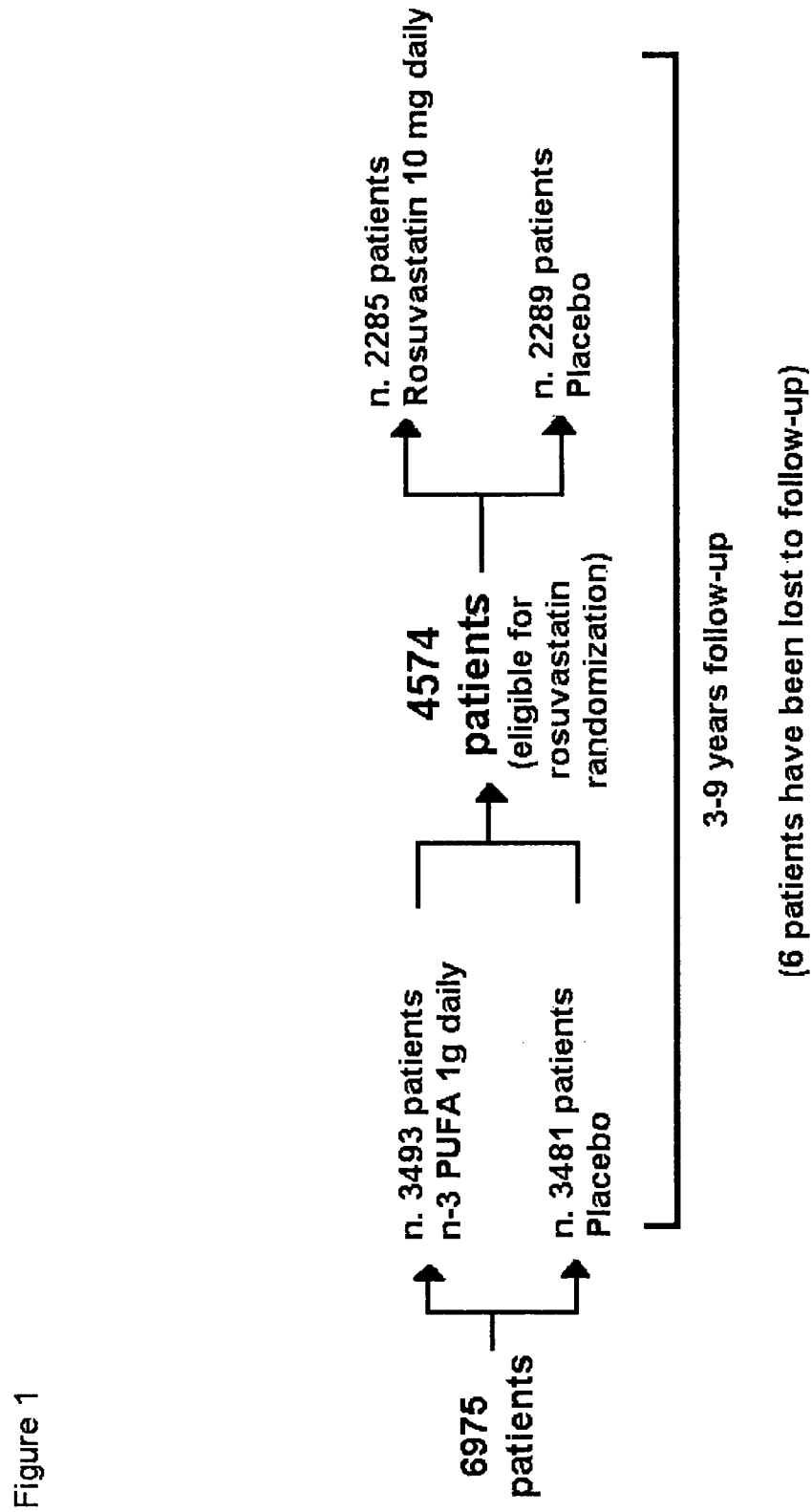
FIG. 1 relates to the trial profile and patients' disposition.

The following Examples further illustrate the invention without limiting it in any way.

EXAMPLES

Example 1

Clinical Trial to Evaluate the Efficacy of a Treatment with n-3 PUFA

Eligible patients were men and women aged 18 years or older with clinical evidence of HF (heart failure) of any etiology classified according to the European Society of Cardiology guidelines as NYHA class II-IV (New York Heart Association Classification) provided that they had had their LVEF (left ventricular ejection fraction or left ventricular function) measured within 3 months prior to enrolment. In the case of a LVEF >40%, the patient had to have been admitted at least once to hospital for HF in the preceding year to meet the inclusion criteria.

All patients gave written informed consent before being enrolled.

An independent Data and Safety Monitoring Board was established to oversee the safety of the patients enrolled in the trial and to monitor the trial's progress. This board had access to all data through an independent statistician. Efficacy in terms of all-cause mortality was monitored using predefined stopping rules.

Patients were randomly assigned, in a double blind way, to receive one capsule per day of 1 g of n-3 PUFA (850-882 mg eicosapentaenoic acid and docosahexaenoic acid as ethyl esters in the average ratio of 1-1.2) or matching placebo. Patients without specific indications or contraindications to statins were also randomized, at the same time, to 10 mg/day of oral rosuvastatin or corresponding placebo (see FIG. 1).

Patients were treated with n-3 PUFA for more than 3.5 years, with a median of 3.9 years.

All treatments of proven efficacy for chronic HF (e.g., ACE-inhibitors, beta-blockers; diuretics, digitalis, spironolactone) were positively recommended.

The rationale and design of the clinical trial above-described has also been reported in "The European Journal of Heart Failure 6 (2004) 635-641". The results obtained at the end of the trial are here reported in the following Tables and Drawings.

Study Endpoints and Predefined Subgroup Analysis

The study was designed with two co-primary endpoints: time to death and time to death or cardiovascular hospitalisation. Secondary outcomes included cardiovascular mortality; cardiovascular mortality or hospitalisation for HF, cardiovascular mortality or hospitalisation for any reason; sudden cardiac death; hospitalisation for any reason; hospitalisation for cardiovascular reasons; hospitalisation for HF; MI (myocardial infarction); stroke.

All the events recorded in the study were adjudicated blindly by an ad-hoc committee on the basis of pre-agreed definitions and procedures.

The effect of study drugs on the combined outcome of all-cause mortality or hospital admission for cardiovascular reasons was evaluated in subgroups of patients defined according to age (above vs below the median value); left ventricular ejection fraction (LVEF %>40% vs<40%) etiology of their HF (ischemic vs non-ischemic); functional capacity (NYHA class II vs III-IV) (see also Eur Heart J, 2001, 22:1527-60); presence of diabetes (yes vs no); and baseline total cholesterol levels (above vs below the median value).

Sample Size and Statistical Aspects

Statistical analyses were performed at an overall significance level of 0.05, adjusted for the two primary endpoints, where the first (time to death) was tested at a two-sided significance level of 0.045 and the second (time to death or cardiovascular hospitalisation) at a significance level of 0.01. Given the correlation between the two co-primary endpoints, the net alpha spending was preserved.

Comparisons of the primary endpoints between treatment groups were performed by means of the log-rank test. To estimate the size of the treatment effect was used the Cox proportional hazards model adjusting for those variables that were found to be unbalanced between randomized groups (p value <0.1). Confidence intervals (CI) of 95.5% and 99% were calculated for the first and second co-primary endpoints, respectively. To estimate the size of the effect on the secondary endpoints (adjusted analysis) and on the composite primary end-point in the pre-specified subgroups, hazard ratios (HR) with 95% (CI) were calculated using a Cox proportional hazards model. All the analyses were conducted in the intention-to-treat population with the exception of a per-protocol analysis on the two co-primary endpoints which was carried out in 4994 patients without major protocol violations who had taken experimental treatments far more than 80% of the time of observation.

Differences between randomized groups in lipids profile across the study (at baseline, 1 and 3 years) were examined by repeated-measures analysis of variance. Whenever the laboratory parameters did not meet the normality assumptions, a log transformation was applied.

Al the analyses were conducted with SAS software, version 8-2.

Results

A total of 6975 patients underwent randomization, 3494 were assigned to receive n-3 PUFA and 3481 to receive placebo (FIG. 1).

The baseline characteristics, including details of background medical treatment, are given in Table 1. The mean age of the patients was 67 years and 42% of them were over 70 years old. Women accounted for 22% of the total population. At study admission, 94%, 65%, and 39% of the patients were being treated with, respectively, blockers of the rennin-angiotensin system, beta-blockers and spironolactone.

TABLE 1

BASELINE CHARACTERISTICS OF PATIENTS

| Patients' characteristics | n-3PUFA (n.3494) | Placebo (n.3481) |
|---|---|---|
| Age (years), mean ± SD | 67 ± 11 | 67 ± 11 |
| Age >70 years, n. (%) | 1465 (41.9) | 1482 (42.6) |
| Females, n. (%) | 777 (22.2) | 739 (21.2) |
| Heart disease risk factors | 27 ± 5 | 27 ± 5 |
| BMI (kg/m$^2$), mean ± SD | | |
| SBP (mmHg), mean ± SD | 126 ± 18 | 126 ± 18 |
| DBP (mmHg), mean ± SD | 77 ± 10 | 77 ± 10 |
| Heart rate (bpm), mean ± SD | 72 ± 13 | 73 ± 14 |
| NYHA class, n. (%) | | |
| II | 2226 (63.7) | 2199 (63.2) |
| III | 1178 (33.7) | 1187 (34.I) |
| IV | 90 (2.6) | 95 (2.7) |
| LVEF (%), mean ± SD | 33.0 ± 8.5 | 33.2 ± 8.5 |
| LVEF >40%, n. (%) | 333 (9.5) | 320 (9.2) |
| Medical history | | |
| Hospitalization for HF in the previous year, n. (%) | 1746 (50.0) | 1638 (47.1) |
| Previous AMI, n. (%) | 1461 (41.8) | 1448 (41.6) |
| Previous stroke, n. (%) | 168 (4.8) | 178 (5.1) |
| Diabetes mellitus, n. (%) | 992 (28.4) | 982 (28.2) |
| CABG, n. (%) | 614 (17.6) | 657 (18.9) |
| PCI, n. (%) | 425 (12.2) | 441 (12.7) |
| ICD, n. (%) | 248 (7.I) | 249 (7.2) |
| Pacemaker, n. (%) | 471 (13.5) | 421 (12.1) |
| History of atrial fibrillation, n. (%) | 682 (19.5) | 643 (18.5) |
| Peripheral vascular disease, n. (%) | 292 (8.4) | 318 (9.I) |
| COPD, n. (%) | 740 (21.2) | 793 (22.8) |
| Neoplasia, n. (%) | 125 (3.6) | 131 (3.8) |
| Cause of heart failure Etiology n. (%) | | |
| Ischemic | 1717 (49.I) | 1750 (503) |
| Dilatative | 1053 (30.1) | 972 (27.9) |
| Hypertensive | 493 (14.1) | 543 (15.6) |
| Other | 107 (3.I) | 89 (2.6) |
| Non detectable/Unknown | 124 (3.6) | 27 (3.6) |
| Physical examination | | |
| Pulmonary rales, n. (%) | 887 (25.4) | 882 (25.3) |
| Third heart sound, n. (%) | 897 (25.7) | 840 (24.1) |

TABLE 1-continued

BASELINE CHARACTERISTICS OF PATIENTS

| | n-3PUFA (n.3494) | Placebo (n.3481) |
|---|---|---|
| Mitral insufficiency, n. (%) | 2222 (63.6) | 2189 (62.9) |
| Aortic stenosis, n. (%) | 82 (2.4) | 61 (1.8) |
| ECG findings | | |
| QRS >120 msec, n. (%), available for 6899 patients | 1171 (33.9) | 1185 (34.4) |
| Atrial fibrillation, n. (%) | 573 (16.4) | 567 (16.3) |
| Pathological Q waves, n. (%) | 797 (22.8) | 807 (23.2) |
| Left ventricular hypertrophy, n. (%) | 660 (18.9) | 678 (19.5) |
| Medical treatment | | |
| ACE-inhibitors/AR Bs, n. (%) | 3268 (93.5) | 3252 (93.4) |
| Beta-blockers, n. (%) | 2275 (65.I) | 2247 (64.6) |
| Spironolactone, n. (%) | 1347 (38.6) | 1393 (40.0) |
| Diuretics, n. (%) | 3127 (89.5) | 3133 (90.0) |
| Digitalis, n. (%) | 1296 (37.I) | 1292 (37.I) |
| Oral anticoagulants, n. (%) | 1027 (29.4) | 982 (28.2) |
| Aspirin, n. (%) | 1673 (47.9) | 1685 (48.4) |
| Other antiplatelet agents, n. (%) | 345 (9.9) | 371 (10.7) |
| Nitrates, n. (%) | 1236 (35.4) | 1236 (35.5) |
| Calcium-channel blockers, n. (%) | 343 (9.8) | 366 (10.5) |
| Amiodarone, n. (%) | 668 (19.I) | 690 (19.8) |
| Statin (open), n. (%) | 778 (22.3) | 801 (23.0) |

BMI = body mass index; SBP = systolic blood pressure; DBF = diastolic blood pressure; NYHA = New York Heart Association; LVEF = left ventricular ejection fraction; HF = heart failure; AMI = acute myocardial infarction; CABG = coronary artery bypass graft; PCI = percutaneous coronary intervention; ICD = implantable cardioverter defibrillator; PVD = peripheral vascular disease; COPD = chronic obstructive pulmonary disease; LVH = left ventricular hypertrophy; ARBs = angiotensin receptor blockers.

Figure 2A:
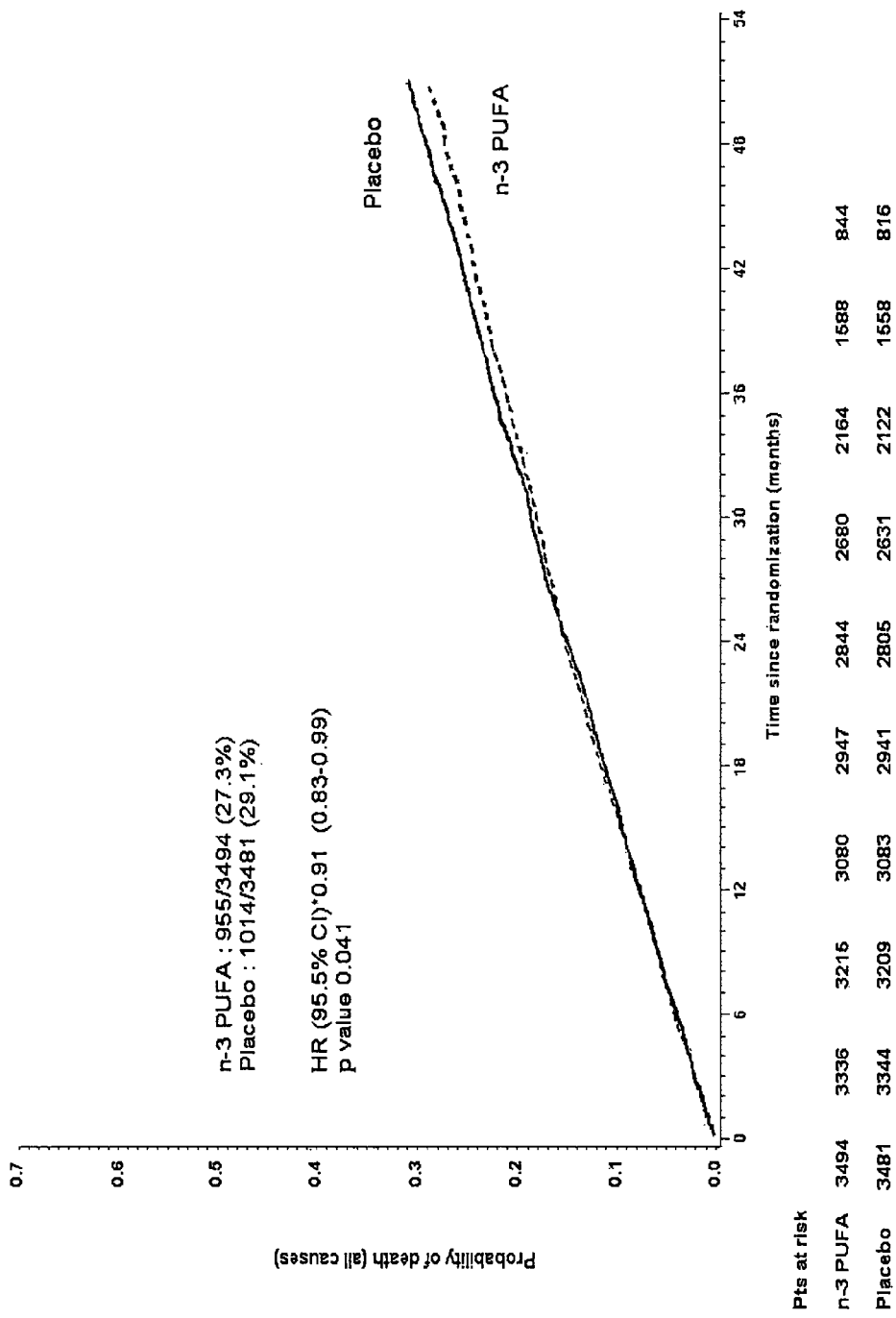
FIG. 2a relates to the Kaplan-Meier curves for time to all-cause death.
Figure 2B:
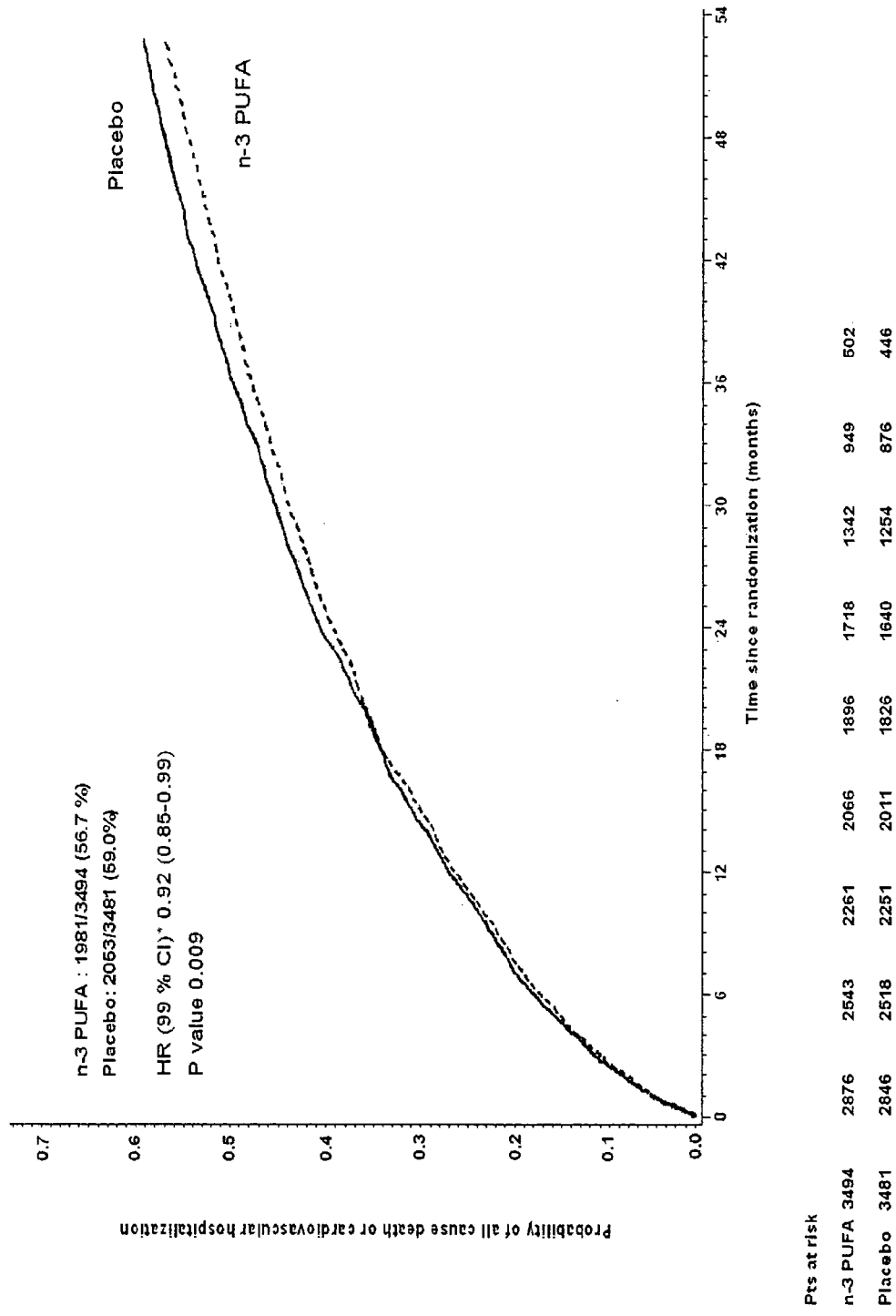
FIG. 2b relates to the Kaplan-Meier curves for time to all-cause death or hospitalisation for cardiovascular reasons.

The main results of the study are presented in FIGS. 2a and 2b for the two co-primary endpoints. In both cases, the Kaplan-Maier curves began to diverge after about 2 years after starting treatment: 955 patients (27.3%) in the n-3 PUFA group and 1014 (29.1%) in the placebo group died from any cause (HR 0.91, 95.5% CI [0.83-0.99], p=0.041); the co-primary outcome of all-cause death or admission to hospital for cardiovascular reasons occurred in 1981 (56.7%) and 2053 (59.0%) patients in the n-3 PUFA and placebo groups, respectively (HR 0.92, 99% CI [0.85-0.99], p=0.009).

Secondary outcomes are shown in Table 2.

TABLE 2

SECONDARY OUTCOMES

| | n-3 PUFA (n.3494) n. (%) | Placebo (n.3481) n. (%) | HR | 95% CI* | Adjusted p value |
|---|---|---|---|---|---|
| Patients who died of a cardiovascular cause | 712 (20.4) | 765 (22.0) | 0.90 | 0.81-0.99 | 0.045 |
| Patients who had a sudden cardiac death | 307 (8.8) | 325 (9.3) | 0.93 | 0.79-1.08 | 0.333 |
| Patients hospitalized | 1986 (56.8) | 2028 (58.3) | 0.94 | 0.88-1.00 | 0.049 |
| Patients hospitalized for a cardiovascular reason | 1635 (46.8) | 1687 (48.5) | 0.93 | 0.87-0.99 | 0.026 |
| Patient hospitalized for HF | 978 (28.0) | 995 (28.6) | 0.94 | 0.86-1.02 | 0.147 |
| Patients who died of a cardiovascular cause or hospitalized for any reason | 2157 (61.7) | 2202 (63.3) | 0.94 | 0.89-0.99 | 0.043 |
| Patients with MI | 107 (3.I) | 129 (3.7) | 0.82 | 0.63-1.06 | 0.121 |
| Patients with stroke | 122 (3.5) | 103 (3.0) | 1.16 | 0.89-1.51 | 0.271 |
| Ischemic | 97 (2.8) | 79 (2.3) | | | |
| Hemorrhagic | 13 (0.4) | 10 (0.3) | | | |
| Not known | 12 (0.3) | 14 (0.4) | | | |

HF = heart failure; MI = myocardial infarction;
*The 95% CI was calculated using a Cox proportional hazards model adjusting for: hospitalisation for HF in the preceding year, prior pacemaker, and aortic stenosis.

The rates of the outcome events in the n-3 PUFA group were lower than in the placebo arm, with stroke being the only exception. The proportions of patients experiencing (a) death for a cardiovascular cause (p=0.045); (b) first hospital admission for any (p=0.049) or cardiovascular cause (p=0.026) after randomization and (c) the combined endpoint of cardiovascular death or hospitalisation for any cause (p=0.043) were significantly lower in the n-3 PUFA group. Sudden cardiac death occurred in 307 (8.8%) of patients allocated to n-3 PUFA and 325 (9.3%) patients in the placebo group (HR 0.93, 95% CI [0.79-1.08], p=0.333). The number of patients who had a first MI after randomization was 107 in the n-3 PUFA group and 129 in the placebo group (p=0.121), stroke occurred in 122 patients assigned to n-3 PUFA and in 103 in the placebo group (p=0.271). First hospitalisation for HF occurred in 978 (28.0%) and 995 (28.6%) patients in the n-3 PUFA and placebo arms, respectively (HR 00.94, 95.5% CI [0.86-1.02], p=0.147).

First hospital admission for ventricular arrhythmias occurred in 97/3494 (2.8%) patients in the n-3 PUFA group vs 132/13481 (3.8%) patients in the placebo group (HR 0.72, 95.5% CI [0.55-0.93], p=0.013).

Causes of death are reported in Table 3.

TABLE 3

CAUSES OF DEATH

|  | n-3 PUFA (n.3494) n. (%) | Placebo (n.3481) n. (%) |
| --- | --- | --- |
| AMI | 20 (0.6) | 25 (0.7) |
| Worsening HF | 319 (9.I) | 332 (9.5) |
| Presumed arrhythmic | 274 (7.8) | 304 (8.7) |
| Stroke | 50 (1.4) | 44 (1.3) |
| Other cardiovascular reasons | 49 (1.4) | 60 (1.7) |
| Neoplasia | 107 (3.I) | 112 (3.2) |
| Other non cardiovascular reasons | 97 (2.8) | 102 (2.9) |
| Not known | 39 (1.I) | 35 (1.0) |

Worsening HF accounted for the majority of deaths, followed by presumed arrhythmic death (defined as documented, or presumed, arrhythmic death or sudden death when a definite cause could not be found). Presumed arrhythmic deaths occurred in 274 (7.8%) patients in the n-3 PUFA group and 304 (8.7%) in the placebo group (HR 0.88, 95% CI [0.75-1.04], p=0.141). Death from worsening HF occurred in 319 (9.1%) and 332 (9.5%) patients in the n-3 PUFA and placebo arms, respectively (HR 0.92, 95% CI [0.79-1.07], p=0.275). The numbers of deaths from non-cardiovascular causes and from cancer were similar in the two treatment groups.

The risk of all-cause death or admission to hospital for cardiovascular reasons was affected by n-3 PUFA in all pre-defined subgroups in a similar way, with no evidence of heterogeneity of the treatment effect (see Table 4).

TABLE 4

PREDEFINED SUBGROUP ANALYSIS: COMPOSITE ENDPOINT OF ALL-CAUSE DEATH OR HOSPITALISATIONS FOR CARDIOVASCULAR REASONS

|  | n-3 PUFA Events/ Patients (%) | Placebo Events/ Patients (%) | HR | 95% CI* |
| --- | --- | --- | --- | --- |
| Age <69 years (median) | 856/1740 (49.2) | 906/1729 (52.4) | 0.92 | 0.84-1.01 |
| Age >69 years (median) | 1125/1754 (64.1) | 1147/1752 (65.5) | 0.96 | 0.88-1.04 |
| LVEF <40% | 1788/3161 (56.6) | 1871/3161 (59.2) | 0.94 | 0.88-0.99 |
| LVEF >40% | 193/333 (58.0) | 182/320 (56.9) | 1.02 | 0.83-1.25 |
| Ischemic etiology | 1079/1717 (62.8) | 1137/1750 (65.0) | 0.95 | 0.87-1.03 |
| Not ischemic etiology | 902/1777 (50.8) | 916/1731 (52.9) | 0.94 | 0.86-1.03 |
| NYHA II | 1130/2226 (50.8) | 1170/2199 (53.2) | 0.93 | 0.86-1.01 |
| NYHA III-IV | 851/1268 (67.1) | 883/1282 (68.9) | 0.96 | 0.87-1.05 |
| Diabetes | 623/992 (62.8) | 660/982 (67.2) | 0.89 | 0.80-0.99 |
| No diabetes | 1358/2502 (54.3) | 1393/2499 (55.7) | 0.96 | 0.89-1.04 |
| Total cholesterol# <188 mg/dL | 1033/1748 (59.1) | 1080/1719 (62.8) | 0.91 | 0.84-0.99 |
| Total cholesterol# >188 mg/dL | 929/1719 (54.0) | 957/1732 (55.3) | 0.96 | 0.88-1.05 |

*The 95% CI was calculated using a Cox proportional hazards model;
Data on total cholesterol were available for 6918 patients;
No significant interactions were shown for any subgroup analysis.
Neither blood pressure nor heart rate was significantly modified by the study treatments.

As expected, plasma levels of triglycerides declined slightly from a median value of 126 mg/dL at baseline to 120 mg/dL, and 119 mg/dL after 1 and 3 years, respectively, in patients allocated to n-3 PUFA treatment, but did not change in the placebo group (interaction time treatment: p<0.0001). No differences were observed in total, HDL- or LDL-cholesterol between patients allocated to n-3 PUFA or placebo.

Summing up, patients enrolled were 6975, 3494 assigned to n-3 PUFA and 3481 to placebo. Mean age was 67 years, etiology was ischemic in 50%. Patients who died, from any cause were 955 (27%) and 1014 (29%) in the n-3 PUFA and placebo group respectively (hazard ratio 0.91, 95.5% confidence interval [0.83-0.99], p=0.041). Co-primary outcome of death or CV hospitalisation was experienced by 1981 (57%) patients in the n-3 PUFA group and 2053 (59%) in the placebo group (hazard ratio 0.92, 99% confidence interval [0.85-0.99], p=0.009). With respect to secondary outcomes, n-3 PUFA reduce the rate of CV death (p=0.045), total hospitalisations (p=0.049) and hospitalisation for CV reasons (p=0.026), as well as the combined end-point of CV death or total hospitalisation (p=0.043). The safety of the drug was excellent.

The results obtained show that the long-term administration of 1 g/day n-3 PUFA was effective in reducing both all-cause mortality and hospitalisations for cardiovascular reasons in the large population of patients included in the trial.

The importance of this benefit must be appreciated tacking into account that: a) it was obtained in a population already intensively treated with recommended therapies; b) it was consistent across all the predefined subgroups, and c) it was further supported by the findings of the per-protocol analysis which are compatible with a greater benefit in fully compliant patients. No adverse effects were noted in the fragile population of symptomatic patients with HF in whom the n-3 PUFA were never been tested, confirming the safety of the drug.

As shown in FIG. 2a and Table 3, out of the absolute risk reduction on total mortality (1.8%), the greatest proportion (50%) was attributed to presumed arrhythmic death. In addition, 47% in the absolute risk reduction on first cardiovascular hospitalisation was due to a reduction of hospitalisations for ventricular arrhythmias.

This treatment provided a beneficial advantage in terms of decreased mortality and cardiovascular hospitalisation on the top of that afforded by already recommended pharmacological treatments. This corresponds to a reduction of 1 death event every 56 patients treated with n-3 PUFA for nearly 4 years.

The invention claimed is:

1. A method of reducing mortality and hospitalization for cardiovascular causes comprising:
   administering an effective amount of a composition comprising omega-3 polyunsaturated fatty acids (n-3 PUFA) for more than 3.5 years to patients with symptomatic HF having left ventricular ejection fraction <40%, diabetes or total cholesterol <200 mg/dl, wherein said n-3 PUFA is a mixture of fatty acids having a content of EPA and DHA comprised between 75% and 95% by weight on the total fatty acids weight.

2. Method of claim 1, wherein said total cholesterol is ≤188 mg/dl.

3. Method of claim 1, wherein the n-3 PUFA is a mixture of fatty acids having a content in EPA and DHA of at least 85% by weight on the total fatty acids weight and the total content of n-3 PUFA is at least 90% by weight on the total fatty acids weight.

4. Method of claim 3, wherein the n-3 PUFA is a mixture of ethyl esters of EPA and DHA in a ratio comprised between 0.9 and 1.5 and the content of EPA ethyl esters is between 40 and 51% and the content of DHA ethyl ester is between 34 and 45 by weight on the total fatty acids weight.

5. Method of claim 1, wherein said effective amount comprises 1 g daily doses of n-3 PUFA.

6. Method of claim 1, wherein n-3 PUFA is administered in combination, separately, substantially simultaneously or sequentially with one or more therapeutic agent.

7. Method of claim 6, wherein the therapeutic agent is selected from the group consisting of: ACE-inhibitors, NEP-inhibitors, ACE/NEP inhibitors, angiotensin I converting enzyme inhibitors, diuretics, positive inotropic drugs, phosphodiesterase inhibitors, arteriolar and venular vasodilators, beta blockers and digital glycosides, or a mixture thereof.

8. Method of claim 6, wherein the therapeutic agent is a statin.

9. Method of claim 8, wherein the statin is selected from the group consisting of: simvastatin, lovastatin, fluvastatin, pravastatin, atorvastatin, cerivastatin, rovastatin and rosuvastatin.

* * * * *